(12) United States Patent
Argiolas et al.

(10) Patent No.: US 6,211,156 B1
(45) Date of Patent: Apr. 3, 2001

(54) PEPTIDES FOR TREATMENT OF ERECTILE DYSFUNCTION

(75) Inventors: Antonio Argiolas, Cagliari (IT); Romano Deghenghi, St. Cergue (CH)

(73) Assignee: Asta Medica A.G., Dresden (DE)

( * ) Notice: Subject to any disclaimer, the term of this patent is extended or adjusted under 35 U.S.C. 154(b) by 0 days.

(21) Appl. No.: 09/437,147

(22) Filed: Nov. 10, 1999

(51) Int. Cl.⁷ .................... A61K 38/05; A61K 38/06; A61K 38/07; C07K 5/06; C07K 5/08
(52) U.S. Cl. .............. 514/18; 514/19; 514/20; 530/330; 530/331; 548/312.1; 548/338.1; 548/496; 564/153; 564/157
(58) Field of Search .................. 530/330, 331; 514/18, 19, 20; 548/312.1, 338.1, 496; 564/153, 157

(56) References Cited

U.S. PATENT DOCUMENTS

| | | | | |
|---|---|---|---|---|
| 5,576,290 | * | 11/1996 | Hadley | 514/11 |
| 5,795,957 | * | 8/1998 | Deghenghi | 530/329 |
| 5,807,985 | * | 9/1998 | Deghenghi | 530/331 |
| 5,932,548 | * | 8/1999 | Deghenghi | 514/15 |
| 5,955,421 | * | 9/1999 | Deghenghi | 514/2 |
| 6,124,263 | * | 9/2000 | Muccioli et al. | 514/17 |

* cited by examiner

*Primary Examiner*—Jeffrey E. Russel
(74) *Attorney, Agent, or Firm*—Pennie & Edmonds LLP

(57) ABSTRACT

The present invention relates to small peptides that cause penile erections in male animals when injected into the paraventricular nucleus of the hypothalamus or when given systemically (intravenously or subcutaneously) to such animals. These peptides are useful in the treatment of erectile dysfunction.

12 Claims, No Drawings

PEPTIDES FOR TREATMENT OF ERECTILE DYSFUNCTION

TECHNICAL FIELD

The present invention relates to peptides that can be administered to treat erectile dysfunction in male animals.

BACKGROUND OF THE INVENTION

The etiology of erectile dysfunction (ED) or impotence, is complex and it is usually divided into the primary or the more frequent secondary dysfunction.

The major cause of ED is vascular but other frequent causes include hormonal disorders, drug use and neurologic disorders.

Treatments for ED can be classified as central or peripheral initiators, central or peripheral conditioners and others. For a comprehensive review of the subject, with discussion on the role of neurotransmitters and neuropeptides, see A. Argiolas and M. R. Melis, Progress in Neurobiology, 47, 235–255 (1995). For classification of treatments, see J. P. W. Heaton et al., Int. J. Impotence Research 9, 115–121(1997).

Among neuropeptides that act centrally to induce penile erection, the best known are ACTH/MSH peptides and oxytocin. These centrally active peptides however are not specific in their action and cannot be used therapeutically because of their important side effects.

Non-peptidyl products are known to be useful for the treatment of ED. Among these, alprostadil ($PGE_1$) is used topically, and apomorphine and sildenafil are administered by sublingual or oral application. All known agents are not devoid important drawbacks such as emetic properties (apomorphine) and cardiovascular side effects (sildenafil).

A treatment is clearly needed that is as specific as possible, causes a minimum of side effects and is easy to administer.

SUMMARY OF THE INVENTION

The present invention relates to the surprising finding that small peptides that do not belong to any of the previously known classes of peptides affecting penile erections can cause penile erections in male animals when injected into the paraventricular nucleus of the hypothalamus or when given systemically (intravenously or subcutaneously) to such animals.

DETAILED DESCRIPTION OF THE PREFERRED EMBODIMENTS

In this description, the following abbreviations are used: D is the dextro enantiomer, Aib is α-Aminoisobutyryl, TXM is tranexamyl (i.e. 4-(aminomethyl) cyclohexanecarbonyl), INIP is isonipecotinyl, GAB is γ-aminobutyryl, IMA is imidazolylacetyl, Mrp is 2-methyl-Trp, β-Nal is β-(2-naphthyl) alanine, Trp is tryptophan, Phe is phenylalanine, Lys is lysine, Arg is arginine, H is hydrogen, and $NH_2$ is terminal amide.

The peptides which are useful in the present invention include those having the general formula:

X-A-B-C-Y-$NH_2$ in which:
X is Aib, TXM, INIP, GAB, H, or IMA;
A is D-Mrp, D-βNal, or D-Trp;
B is D-Mrp, D-βNal, D-Trp, or is not present;
C is D-Mrp, Phe, or is not present;
Y is Lys or Arg;
in which:
Preferred peptides of the present invention include:

GAB-D-Mrp-D-βNal-Phe-Lys-$NH_2$;

GAB-D-Mrp-D-Mrp-D-Mrp-Lys-$NH_2$;

GAB-D-Mrp-D-βNal-Phe-Arg-$NH_2$; and

GAB-D-Mrp-D-Mrp-Lys-$NH_2$.

Any pharmaceutically acceptable salts of the peptides of the present invention can be used, if desired. Such salts would include but are not limited to organic or inorganic addition salts such as, for example, hydrochloride, hydrobromide, phosphate, sulfate, acetate, succinate, ascorbate, tartrate, gluconate, benzoate, malate, fumarate, stearate, and pamoate salts.

The above peptides can be conveniently prepared according to the usual methods of peptide chemistry by solid phase synthesis using Fmoc-aminoacids (Fmoc is fluorenylmethoxy carbonyl) as described Atherton and Sheppard "*Solid Phase Peptide Synthesis*" (IRL Press at Oxford University Press, 1989), or in J. Jones "*The Chemical Synthesis of Peptides*" (Clarendon Press, Oxford, 1994).

The solid-phase synthesis starts from the C-terminal end of peptide. A suitable starting material can be prepared, for example, by attaching the required protected alpha-amino acid to a chloromethylated resin, a hydroxymethylated resin, a benzhydrylamine resin (BHA), or to a para-methylbenzhydrylamine resin (p-Me-BHA). As an example, an available chloromethylated resin is BIOBEADS® SX 1 by BioRad Laboratories, Richmond, Calif. The preparation of the hydroxymethyl resin is described by Bodansky et al., Chem. Ind. (London) 38, 15997 (1966). The BHA resin is described by Pietta and Marshall, Chem. Comm., 650 (1970) and is commercially available by Peninsula Laboratories Inc., Belmont, Calif.

After the starting attachment, the protecting group of the alpha-amino acid can be removed by means of different acid reagents, comprising trifluoroacetic acid (TFA) or hydrochloric acid (HCl) dissolved in organic solvents at room temperature. After the removal of the protecting group of the alpha-amino acid, the remaining protected amino acids can be coupled step by step in the desired order. Each protected amino acid can generally be reacted in excess of about three times using a suitable carboxyl activating group, such as dicyclohexylcarbodiimiide (DCC) or diisopropylcarbodiimide (DIC) dissolved, for example, in methylene chloride (CH2Cl2), dimethylformamide (DMF) or their mixtures. After the desired aminoacidic sequence has been completed, the desired peptide can be cleaved from the supporting resin by treatment with a reagent such as hydrogen fluoride (HF) which cleaves not only the peptide from the resin, but also the protecting groups of the lateral chains. When a chloromethylated resin or a hydroxymethylated resin is used, the treatment with HF leads to the formation of the terminal acid peptide in free form. When a BHA or p-Me-BHA resin is used, treatment with HF directly leads to the formation of the terminal amide peptide in free form.

The above peptides can be administered systemically, sublingually, buccally, orally intranasally, intrapulmonary or intraocularly at doses between 0.02 and 2 mg/kg of body weight appropriately formulated with pharmaceutically acceptable excipients or in the form of aqueous solutions or as solid powders in micronized form. Other dosage forms, though not specifically listed, are known to those skilled in the art and are within the scope of the present invention.

Medicaments useful for treating erectile dysfunction or for inducing an erection in a male animal including a human can comprise a peptide of the present invention or a pharmaceutically acceptable salt thereof, or combinations of peptides of the present invention or pharmaceutically acceptable salts thereof, optionally, in admixture with a carrier, excipient, vehicle, diluent, matrix, or delayed release coating. Examples of such carriers, excipients, vehicles, and diluents, can be found in Remingtons Pharmaceutical Sciences, 18$^{th}$ edition, A. R. Gennaro, Ed., Mack Publishing Company, Easton, Pa., 1990.

EXAMPLES

The following examples are only provided as being illustrative of preferred embodiments of the present invention and are not intended to limit the breadth and scope of the invention as is readily understood by those skilled in the art.

The following examples illustrate the activity of four peptides which are representative of some preferred embodiments of the invention:

| | |
|---|---|
| GAB-D-Mrp-D-βNal-Phe-Lys-NH$_2$ | (1) |
| GAB-D-Mrp-D-Mrp-D-Mrp-Lys-NH$_2$ | (2) |
| GAB-D-Mrp-D-βNal-Phe-Arg-NH$_2$ | (3) |
| GAB-D-Mrp-D-Mrp-Lys-NH$_2$ | (4) |

Prior to formulation for the appropriate biological test, the synthesized peptides were purified to a purity of >95% by column chromatography.

Testing Procedures:

The procedure described by M. R. Melis et al., *European Journal of Pharmacology* 328, 115–123 (1997) was essentially adapted as follows:

Animals:

Male Sprague Dawley rats (200–220 g) (Charles River, Como, Italy) were used in all the experiments. The animals were caged in groups of 4–6 at 24° C., 60% humidity, the lights were on from 07:00 to 19:00 h with water and standard laboratory food ad libitum. The experiments were performed between 09:00 and 13:00 h.

Pharmaceutical Compounds:

[d(CH$_2$)$_5$Tyr(Me)$^2$Orn$^8$]vasotocin and ω-conotoxin-GVIA were purchased from Peninsula Eur. Ltd. (St. Helen, Merseyside, UK), N$^G$-nitro-1-arginine methyl ester and dizolcipine (MK-801) from Sigma (S. Louis, Mo., USA), cis-flupentixol-HCl from RBI (Natick, Mass., USA) and morphine-HCl from SALARS (Como, Italy).

Microinjections into the Lateral Ventricles (i. c. v.) and into the Paraventricular Nucleus of the Hypothalamus (PVN):

Stainless-steel guide cannulas (22 gauge, 0.71 mm) aimed unilaterally at the PVN were stereotaxically implanted (David Kopf Instruments, USA) under chloral hydrate anaesthesia two days before the experiments (coordinates: 0.2 mm anterior to bregma, 0.4 lateral to midline and 2.0 mm ventral to dura). Each rat was used only once. The same guide cannula was used for i.c.v. and PVN injections.

For i.c.v. injections, all substances were injected in a volume of 10 μl of saline in 1 minute, via an internal cannula (28 gauge) which extended 1 mm below the tip of the guide cannula and connected by polyethylene tubing to a 10 μl Hamilton syringe driven by a micrometric screw. Controls received 10 μL of saline. After injection, the tip of the cannula was left in the injection site for 30 seconds to allow the spread of the injected solution.

For PVN injections, all substances were injected in a volume of 0.3 μl of saline, in 2 minutes through an internal cannula that extended 5.3 mm below the tip of the guide cannula and connected by a polyethylene tubing to a 10 μl Hamilton syringe driven by a Stoelting microinfusion pump. Controls received 0.3 μl of saline in the PVN. After microinjection, the tip of the cannula was left in the injection site for 30 seconds to allow the spread of the injected solution.

Behavioral Studies:

When dose-curves were performed, each peptide or saline was microinjected over a 2-minute period into the PVN of rats implanted with chronic guide cannulas. Saline, ω-conotoxin, morphine, [d(CH$_2$)$_5$Tyr(Me)$^2$-Orn$^8$]-vasotocin, L-NAME MK 801 or cis-flupentixol was injected over a 2-minute period, 10 or 15 minutes before saline, into the PVN of rats implanted with chronic guide cannulas. L-NAME was injected i.c.v. over a 1 minute period, 10 or 15 minutes before saline or the test peptide.

Shortly after treatment, the animals were placed individually into Plexiglas cages (30×30×30 cm) and observed for 60 minutes, during which time penile erection episodes were counted by an observer who was not aware of the treatments to eliminate subjective evaluations.

Histology:

At the end of the experiments, the animals were killed by decapitation, the brains were immediately removed and stored in 2% aqueous formaldehyde for 10–12 days. To localize the injection site, 50-μm transverse brain sections, prepared by means of a freezing microtome, were stained with Neutral Red and inspected on a phase-contrast microscope. The injection site was localized by following the internal cannula tract through a series of brain sections. Only those animals found to have the internal cannula tip positioned correctly i.c.v. or in the PVN were included for the statistical evaluation of the results.

Statistics:

Statistical evaluation of the results was performed by one-way analysis of variance (ANOVA) for repeated measures, followed by Duncan's multiple range test for the comparison of differences among multiple groups. Student's t-test was used to compare differences between two groups. A $p<0.025$ was considered significant.

Example 1

Effect on Spontaneous Penile Erections of the Injecting the Instant Peptides into the PVN All of the four peptides tested injected into the PVN were found able to increase dose-dependently the number of spontaneous penile erection episodes in male rats. The minimal effective dose was 20 to 50 ng that increases the response in more than 70% of the treated animals. The maximal effect was found with 2 to 5 μg that induced the response in more than 90% of the animals. After an active dose, the response began 5–8 minutes after treatment and lasted for 50–60 minutes. Each episode of penile erection lasted 0.5–2 minutes and was associated with or followed by genital grooming. The above doses also increased the number of spontaneous yawning episodes, although this effect was not so marked as that on penile erection and a clear dose-dependence was not found.

Example 2
Effect of [d(CH$_2$)sTyr(Me)$^2$-Orn$^8$]-Vasotocin on Induced Penile Erection of Instant Peptides

[d(CH$_2$)$_5$Tyr(Me)$^2$-O$^8$]-Vasotocin, an Oxytocin Receptor Antagonist, (0.1, 0.5 and 1 μg) injected i.c.v. 10 minutes before the instant peptides reduced dose-dependently the increase in the number of penile erection episodes induced by injecting 2 μg of the instant peptides into the PVN. In contrast, the oxytocin receptor antagonist (0.1, 0.5 and 1 μg) was ineffective when injected into the PVN 10 minutes before the instant peptides.

Example 3
Effect of L-NAME on Penile Erection Induced by Instant Peptides

L-NAME, an inhibitor of NO synthase, (10–20 μg) injected into the PVN 10 minutes before the instant peptides, reduced in a dose dependent manner penile erections induced by injecting 2 μg of the test peptides into the PVN. A similar prevention was observed when L-NAME was injected i.c.v. at doses of 75 and 150 μg 10 minutes before injecting 2 μg of the test peptides into the PVN.

Example 4
Effect of ω-Conotoxin-GVIA on Test Peptide Induced Penile Erection The N-type Ca$^{2+}$ channel blocker ω-conotoxin-GVIA (2 and 5 μg) injected into the PVN 10 minutes before injecting 2 μg of the test peptides into the PVN reduced penile erection.

Example 5
Effect of Morphine on Test Peptides Induced Penile Erection

The opiate morphine (1,5 and 10 μg) injected into the PVN 15 minutes before the test peptides reduced in a dose-dependent manner penile erections induced injecting 2 μg of the test peptides into the PVN.

Example 6
Effect of MK-801 or Cis-Flupentixol on Test Peptides Induced Penile Erection The NMDA excitatory amino acid receptor antagonist MK 801 (1 μg) or the dopamine receptor antagonist cis-flupenthixol (10 μg) injected into the PVN 15 minutes before the test peptides did not modify the penile erection.

Example 7
Systemic Administration

Penile erection was observed in all animals in which the instant peptides were injected (50 μg/50 μl) subcutaneously or in the jugular vein.

What is claimed is:

1. A method for causing penile erection in a male animal, which comprises administering to said animal a peptide having the following formula:

X-A-B-C-Y-NH$_2$ wherein:
  X is α-aminoisobutyryl, tranexamyl (i.e. 4-(aminomethyl) cyclohexanecarbonyl), isonipecotinyl, γ-aminobutyryl, hydrogen, or imidazolylacetyl;
  A is D-2-methyl-tryptophan, D-β-(2-naphthyl) alanine, or D-tryptophan;
  B is D-2-methyl-tryptophan, D-β-(2-naphthyl) alanine, D-tryptophan, or is absent;
  C is D-2-methyl-tryptophan, phenylalanine, or is absent;
  Y is lysine or arginine;
wherein D stands for the dextro isomer; or a pharmaceutically acceptable addition salt of the peptide, in an amount effective to cause said erection.

2. The method of claim 1 in which the peptide is administered intranasally, intrapulmonary or intraocularly.

3. The method of claim 1 in which the peptide is administered buccally, sublingually or orally.

4. The method of claim 1 wherein the peptide is:

GAB-D-Mrp-D-βNal-Phe-Lys-NH$_2$;

GAB-D-Mrp-D-Mrp-D-Mrp-Lys-NH$_2$;

GAB-D-Mrp-D-βNal-Phe-Arg-NH$_2$;

GAB-D-Mrp-D-Mrp-Lys-NH$_2$;

GAB-D-Mrp-Lys-NH$_2$;

GAB-D-Trp-D-Trp-Lys-NH$_2$;

or pharmaceutically acceptable salts thereof.

5. The method of claim 1 wherein the peptide is administered at a dose of between 0.2 and 2 mg/kg of body weight of the animal.

6. The method of treating erectile dysfunction in a male animal, which comprises administering to said animal a peptide having the following formula:

X-A-B-C-Y-NH$_2$ wherein
  X is α-aminoisobutyryl, tranexamyl (i.e. 4-(aminomethyl) cyclohexanecarbonyl), isonipecotinyl, γ-aminobutyryl, hydrogen, or imidazolylacetyl;
  A is D-2-methyl-tryptophan, D-β-(2-naphthyl) alanine, or D-tryptophan;
  B is D-2-methyl-tryptophan, D-β-(2-naphthyl) alanine, D-tryptophan, or is absent;
  C is D-2-methyl-tryptophan, phenylalanine, or is absent;
  Y is lysine or arginine;
wherein D stands for the dextro isomer; or a pharmaceutically acceptable addition salt of the peptide, in an amount effective to cause said erection.

7. The method of claim 6 in which the peptide is administered intranasally, intrapulmonary or intraocularly.

8. The method of claim 6 in which the peptide is administered buccally, sublingually or orally.

9. The method of claim 6 wherein the peptide is:

GAB-D-Mrp-D-βNal-Phe-Lys-NH$_2$;

GAB-D-Mrp-D-Mrp-D-Mrp-Lys-NH$_2$;

GAB-D-Mrp-D-βNal-Phe-Arg-NH$_2$;

GAB-D-Mrp-D-Mrp-Lys-NH$_2$;

GAB-D-Mrp-Lys-NH$_2$;

GAB-D-Trp-D-Trp-Lys-NH$_2$;

or pharmaceutically acceptable salts thereof.

10. The method of claim 6 wherein the peptide is administered at a dose of between 0.2 and 2 mg/kg of body weight of the animal.

11. A peptide having the formula:

GAB-D-Mrp-D-βNal-Phe-Arg-NH$_2$;

GAB-D-Mrp-D-Mrp-Lys-NH$_2$;

GAB-D-Mrp-Lys-NH$_2$;

GAB-D-Trp-D-Trp-Lys-NH$_2$;

and pharmaceutically acceptable addition salts thereof.

12. A pharmaceutical composition comprising the peptide of claim 11 and a pharmaceutically acceptable carrier.

* * * * *